US007691336B2

(12) United States Patent
Westring (10) Patent No.: US 7,691,336 B2
(45) Date of Patent: Apr. 6, 2010

(54) DEVICES AND SYSTEMS FOR DISPENSING VOLATILE MATERIALS

(75) Inventor: Brice Daniel Westring, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 851 days.

(21) Appl. No.: 10/447,755

(22) Filed: May 29, 2003

(65) Prior Publication Data

US 2004/0009103 A1 Jan. 15, 2004

Related U.S. Application Data

(63) Continuation-in-part of application No. 09/904,019, filed on Jul. 12, 2001, now abandoned, and a continuation-in-part of application No. 09/730,226, filed on Dec. 5, 2000, now Pat. No. 6,581,915, and a continuation-in-part of application No. 09/730,333, filed on Dec. 5, 2000, now abandoned, and a continuation-in-part of application No. 09/730,261, filed on Dec. 5, 2000, now abandoned.

(51) Int. Cl.
*A62B 7/08* (2006.01)
*A61L 9/00* (2006.01)
*B01D 47/00* (2006.01)
*F02M 37/00* (2006.01)
*F02M 69/02* (2006.01)

(52) U.S. Cl. ........................ 422/125; 422/120; 422/123; 422/5; 261/26

(58) Field of Classification Search ................. 422/125, 422/123, 120, 5, 117; 261/107; 219/438
See application file for complete search history.

(56) References Cited

U.S. PATENT DOCUMENTS 3,410,488 A 11/1968 Sugimura
3,872,280 A * 3/1975 Van Dalen .................. 392/390

(Continued)

FOREIGN PATENT DOCUMENTS

CA 2222838 7/1996

(Continued)

OTHER PUBLICATIONS

U.S. Appl. No. 60/210,247; Ketcha et al., filed Jun. 8, 2000.*

(Continued)

*Primary Examiner*—Elizabeth L McKane
*Assistant Examiner*—Regina Yoo
(74) *Attorney, Agent, or Firm*—Julia A. Glazer; Amy I Ahn-Roll; Jeffrey V. Bamber (57) ABSTRACT

Devices and systems and methods for dispensing volatile materials are disclosed. In one embodiment, the system includes a device for emitting volatile materials from an article of manufacture that contains volatile compositions. In such an embodiment, a portion of the device and a portion of the article together define an air flow path for emitting the volatile materials. The device may have various features, including: a heater that is movable with a spring; safety features; and a closed-loop heater temperature feedback system. The device can have placement instructions associated therewith for proper operation of the device.

3 Claims, 8 Drawing Sheets

U.S. PATENT DOCUMENTS

| | | | |
|---|---|---|---|
| 4,549,250 A | 10/1985 | Spector | |
| 4,588,874 A | 5/1986 | Napierski | |
| 4,603,030 A | 7/1986 | McCarthy | |
| 4,629,604 A | 12/1986 | Spector | |
| 4,631,387 A * | 12/1986 | Glucksman | 392/390 |
| 4,645,353 A | 2/1987 | Kavoussi et al. | |
| 4,695,434 A | 9/1987 | Spector | |
| 4,714,984 A | 12/1987 | Spector | |
| 4,743,406 A | 5/1988 | Steiner et al. | |
| 5,023,020 A | 6/1991 | Machida et al. | |
| 5,071,621 A | 12/1991 | Tokuhiro et al. | |
| 5,163,616 A | 11/1992 | Bernarducci et al. | |
| 5,167,877 A | 12/1992 | Pai | |
| 5,220,636 A | 6/1993 | Chang | |
| 5,234,162 A | 8/1993 | Sullivan | |
| 5,397,510 A * | 3/1995 | Clark | 261/26 |
| 5,480,591 A | 1/1996 | Lagneaux et al. | |
| 5,518,790 A | 5/1996 | Klocke et al. | |
| 5,565,148 A | 10/1996 | Pendergrass, Jr. | |
| 5,662,835 A | 9/1997 | Collingwood | |
| 5,805,768 A | 9/1998 | Schwartz et al. | |
| 5,887,118 A | 3/1999 | Huffman et al. | |
| 5,972,290 A | 10/1999 | De Sousa | |
| 6,024,783 A | 2/2000 | Budman | |
| 6,136,277 A | 10/2000 | Nardini | |
| 6,152,829 A | 11/2000 | Jaidka | |
| 6,179,275 B1 | 1/2001 | Lagneaux et al. | |
| 6,325,475 B1 * | 12/2001 | Hayes et al. | 347/2 |
| 6,357,726 B1 | 3/2002 | Watkins | |
| 6,371,453 B1 * | 4/2002 | Hunter | 261/107 |
| 6,390,453 B1 | 5/2002 | Frederickson et al. | |
| 6,406,004 B1 | 6/2002 | Ude | |
| 6,413,476 B1 * | 7/2002 | Barnhart | 422/124 |
| 6,548,025 B1 * | 4/2003 | Rasouli et al. | 422/123 |
| 6,581,915 B2 | 6/2003 | Bartsch et al. | |
| 6,834,847 B2 | 12/2004 | Bartsch et al. | |
| 2002/0005437 A1 * | 1/2002 | Ketcha et al. | 239/13 |
| 2002/0058595 A1 | 5/2002 | Kaiser | |
| 2002/0066798 A1 | 6/2002 | Laudamiel-Pellet et al. | |
| 2002/0066967 A1 | 6/2002 | Bartsch et al. | |
| 2002/0068009 A1 | 6/2002 | Laudamiel-Pellet et al. | |
| 2002/0068010 A1 | 6/2002 | Bush et al. | |
| 2002/0122751 A1 * | 9/2002 | Sinaiko et al. | 422/186 |
| 2002/0158351 A1 | 10/2002 | Wohrle | |
| 2003/0164557 A1 | 9/2003 | Chung et al. | |
| 2003/0206839 A1 * | 11/2003 | Taylor et al. | 422/186.04 |
| 2004/0007787 A1 | 1/2004 | Kvietok et al. | |
| 2004/0096369 A1 * | 5/2004 | Daoting | 422/124 |
| 2005/0016985 A1 * | 1/2005 | Haas et al. | 219/438 |

FOREIGN PATENT DOCUMENTS

| | | |
|---|---|---|
| EP | 0 295 129 A1 | 12/1988 |
| EP | 0 836 856 A2 | 4/1998 |
| EP | 1 205 192 A1 | 5/2002 |
| EP | 1 205 193 A1 | 5/2002 |
| EP | 1 205 194 A1 | 5/2002 |
| EP | 1 205 195 A1 | 5/2002 |
| EP | 1 304 127 A1 | 4/2003 |
| GB | 2253954 A * | 9/1992 |
| GB | 2 349 089 A | 10/2000 |
| WO | WO 97/02076 | 1/1997 |
| WO | WO 99/08174 | 2/1999 |
| WO | WO 00/12143 * | 3/2000 |
| WO | WO 00/15268 | 3/2000 |
| WO | WO 00/15269 | 3/2000 |
| WO | WO 01/07093 A1 | 2/2001 |
| WO | WO 01/19417 A1 | 3/2001 |
| WO | WO 02/38192 A1 | 5/2002 |
| WO | WO 02/38193 A1 | 5/2002 |
| WO | WO 02/38194 A1 | 5/2002 |
| WO | WO 02/38195 A1 | 5/2002 |
| WO | PCT/US2004/016396 | 9/2004 |

OTHER PUBLICATIONS

Aromajet Press Release, "Aromajet.com Demonstrates Proof-of-Concept Aroma Generation System for Game Environments", on Aromajet.com web site Jan. 19, 2001.

Digiscents Products, "Our Product 'Sweet'", on DigiScents web site Jan. 19, 2001.

Norelco Consumer Products Company, "Aromatherapy System AT100" instructions, copyright 1996.

Ultrascent Products, "The Ultimate Aromatherapy Diffuser—UltraScent the Only Multi-scent Aromatherapy Diffuser", on Bunny Moony Enterprise's web site Aug. 5, 2000.

Homedics, Inc., Package for Body Basics TM Sound and Aroma Therapy Enviraspa TM, HoMedics, Inc., Commerce Township, MI, USA, copyright 1998.

Homedics, Inc., Package for Aromalamp TM Color and Aromatherapy Diffuser Model ARM-3, HoMedics, Inc., Commerce Township, MI, USA, copyright 1999.

Philips Electronics of North America Corporation, Package for PHILIPS Natural Aromas Aromatherapy System AT500, Philips Electronics North America Corporation, Stamford, CT, USA, copyright 1999.

Sunbeam Products, Inc., Package for Sunbeam(R) Health At Home (R) Air Cleaner and Freshener, Sunbeam Products, Inc., Boca Raton, FL, USA, copyright 1999.

The Yankee Candle Company, Inc., Package for Garden Favorites TM Scented Tea Light Candles, The Yankee Candle Company, Inc., South Deerfield, MA, USA, date of first publication unknown, obtained Jul. 27, 2001.

S.C. Johnson & Son, Inc., Glade(R) Duet (R) 2 in 1 gel + spray newspaper advertisement and coupon, S.C. Johnson & Son, Inc., Del Rio, TX, USA, copyright 2001.

Osmooze.Com, web pages showing PAD (Personal Aroma Diffuser) USB, Osmooze.com, France, 2001.

* cited by examiner

DEVICES AND SYSTEMS FOR DISPENSING VOLATILE MATERIALS

CROSS-REFERENCE TO RELATED CASES

This application is a continuation-in-part of U.S. patent application Ser. No. 09/904,019 filed on Jul. 12, 2001 now abandoned and U.S. patent application Ser. No. 09/730,226 now U.S. Pat. No. 6,581,915; Ser. No. 09/730,261 now abandoned: and Ser. No. 09/730,333 now abandoned all filed Dec. 5, 2000, the disclosures of which are incorporated by reference herein.

FIELD OF THE INVENTION

The present invention relates to devices and systems for dispensing multiple volatile materials, including but not limited to scents into the environment.

BACKGROUND OF THE INVENTION

Devices are currently available for dispensing volatile materials, such as a single scent into a room and in automobiles. Examples of devices for dispensing a single scent into a room include GLADE PLUG INS® plug in room fresheners manufactured by S. C. Johnson. Devices capable of dispensing scented materials are also described in the patent literature. Examples of such devices are described in: U.S. Pat. Nos. 4,549,250; 4,714,984, 4,695,434; 4,629,604; and 5,805,768; and in PCT Publication WO 97/02076 and Canadian Patent Application 2,222,838; PCT Publication WO 00/121143; and U.S. Patent Publications 2002/0066798, 2002/0066967, 2002/0068009, and 2002/0068010. The search for improved devices and systems, however, has continued.

SUMMARY OF THE INVENTION

This invention relates to devices and systems for dispensing volatile materials into the environment. Several non-limiting embodiments are described herein, as are several components of the system, each of which may constitute an invention in its own right or together with other components.

In one embodiment, the system for dispensing volatile materials includes an apparatus, such as a dispensing device and an article of manufacture containing one or more volatile materials for use in conjunction with the dispensing device. The dispensing device can be any device that is capable of dispensing scents or aromatic materials that are either contained in or on the dispensing device, or contained in or on an article of manufacture that is intended to be used in conjunction with the dispensing device. In such an embodiment, a portion of the device and a portion of the article together define an air flow path for emitting the volatile materials. The device may have various features, including: a heater that is movable with a spring; safety features; and a closed-loop heater temperature feedback system. The device can have placement instructions associated therewith for proper operation of the device.

Numerous other embodiments are also possible, including, but not limited to those described in the following detailed description.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

I. Introduction (The Dispensing System and Apparatus).

This invention relates to devices and systems for dispensing volatile materials into the environment. In several embodiments, this invention relates to devices and systems for dispensing multiple scents into the environment. Several non-limiting embodiments are described herein, as are several components of the system, each of which may constitute an invention in its own right or together with other components. The volatile materials can be supplied to various facilities, which include but are not limited to rooms, houses, hospitals, offices, theaters, buildings, and the like, or into various vehicles such as trains, subways, automobiles, airplanes and the like.

The term "volatile materials" as used herein, refers to a material that is vaporizable. The terms "volatile materials", "aroma", and "scents", as used herein, include, but are not limited to pleasant or savory smells, and, thus, also encompass scents that function as insecticides, air fresheners, deodorants, aromacology, aromatherapy, or any other odor that acts to condition, modify, or otherwise charge the atmosphere or to modify the environment. It should be understood, however, that perfumes, aromatic materials, and scents will often be comprised of one or more volatile materials (which may form a unique and/or discrete unit comprised of a collection of volatile materials).

In one embodiment, the system for dispensing volatile materials comprises one or more components containing one or more scents or aromatic materials. In such an embodiment, the system preferably comprises a dispensing device, such as a device and one or more aromatic material-containing articles of manufacture, or "scent-containing articles of manufacture", which may be provided in the form of fragrance "cartridges". Each cartridge can provide a single volatile composition, or a combination of different volatile materials, such as a combination of different scented materials. It should be understood, however, that the present invention is not limited to devices that are capable of emitting multiple scents, since various aspects of the invention are believed to be novel even when used on devices capable of emitting a single scent, or other type of volatile composition.

Figure 1:
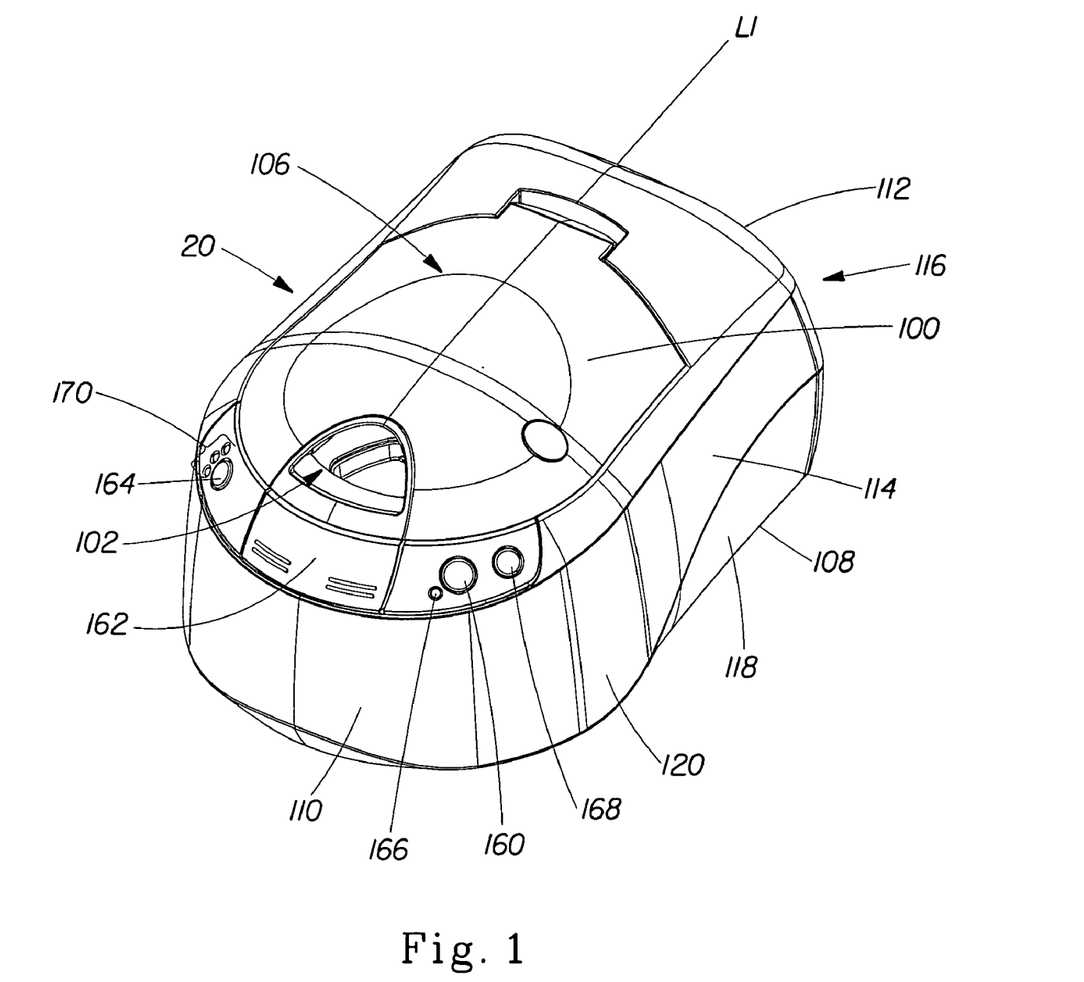
FIG. 1 is a perspective view of one embodiment of a device with the cartridge inserted and the top cover in a closed position.
Figure 3:
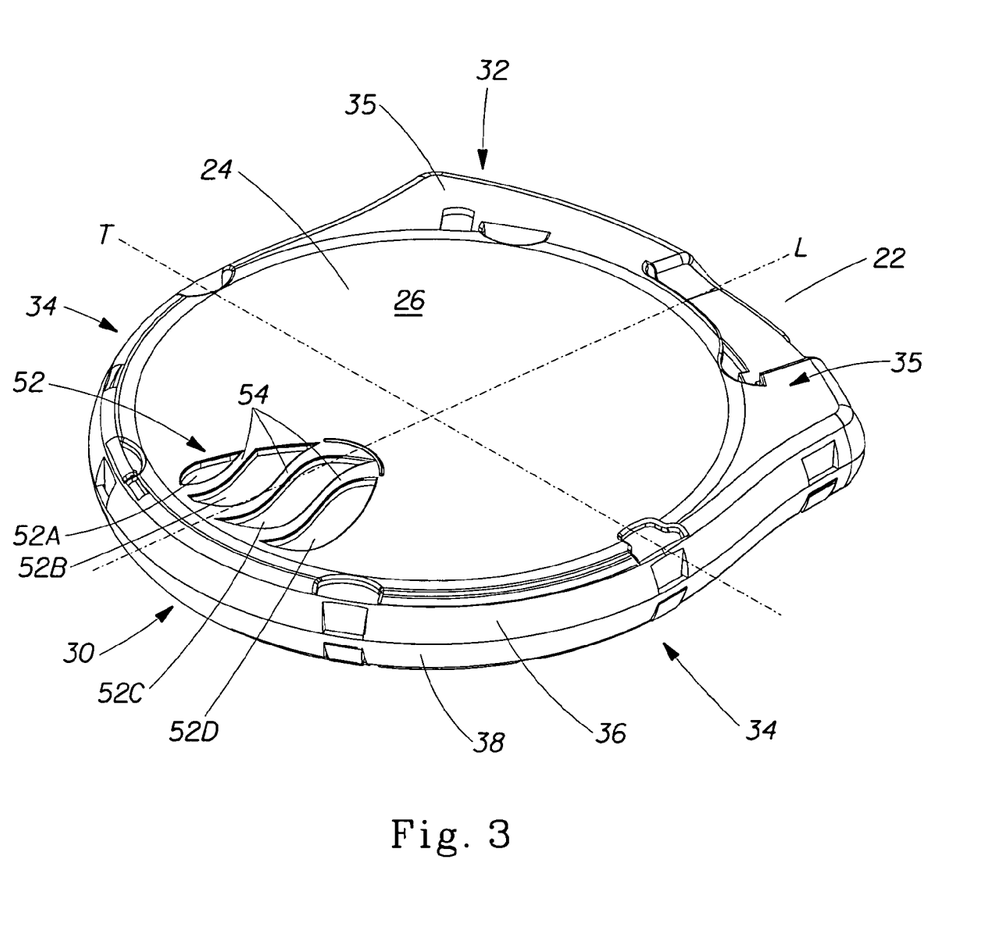
FIG. 3 is a perspective view of one embodiment of a cartridge.
Figure 4:
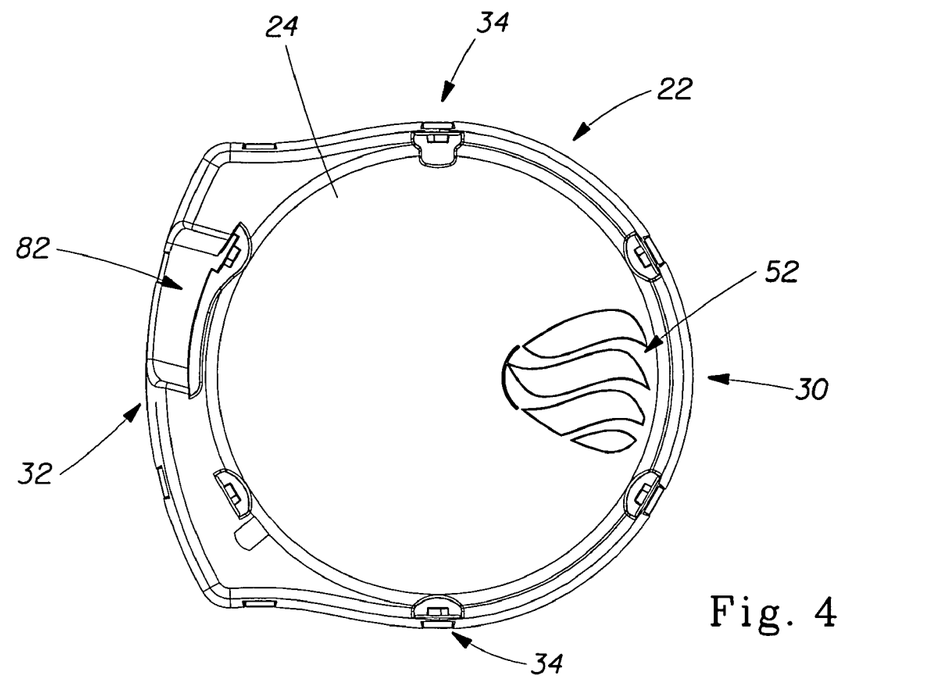
FIG. 4 is a top plan view of the cartridge shown in FIG. 3.

FIGS. 1 and 3 show one non-limiting embodiment of the system of the components for dispensing volatile materials into the environment. The system shown in these figures comprises an apparatus (or "diffuser", "dispensing device", or simply "device") 20 and a replaceable multiple compartment volatile composition-containing article of manufacture, such as cartridge 22. The drawings show one non-limiting example of the device and the volatile composition-containing article of manufacture. The control buttons for the device are described in greater detail below. The system of the present invention (that is, the device and cartridge) can be provided in many other suitable configurations.

II. The Volatile Composition-Containing Article of Manufacture.

FIG. 3 shows one non-limiting embodiment of the volatile composition-containing article of manufacture in the form of cartridge 22 as it appears when it is removed from the device 20. The cartridge 22 can contain a single volatile composition, such as a scented material, or multiple volatile compositions (e.g., multiple scented materials and/or other types of volatile compositions). The cartridge 22 has a longitudinal centerline L, and a transverse centerline T.

The cartridge 22 comprises a housing portion (or shell) 24, which has a top surface 26, a bottom surface 28, a front end 30, a rear end 32, and sides 34. The cartridge 22 can be of any suitable configuration. In other embodiments, the volatile compositions may be contained in or on an article that does not resemble the cartridge shown in the drawings. The term "cartridge" as used herein, is not limited to articles that are in the form of cases or cassettes. For example, the volatile compositions could be provided in or on an article that resembles a disk, such as a compact disk (CD), rather than the article shown in the drawings. In addition, it should be understood that whenever the term "cartridge" is used herein, this is done merely for the purpose of describing the structure shown in the drawings, and anything that is described relative to the cartridge will also be applicable to other types and configurations of articles of manufacture.

In the embodiment shown in the drawings, the cartridge 22 has a disk-like configuration. When viewed from above, the cartridge 22 has a generally circular configuration with a protruding region 35 at the rear end 32 thereof. The cartridge 22 has a front half with a configuration that resembles a half circle when viewed from above. The rear half of the cartridge 22 resembles a half circle with a region 35 protruding from the rear end 32 of the cartridge 22. The sides 34 of the cartridge on the rear half of the cartridge in the protruding region 35 are curved slightly concave inward. This protruding region 35 can be used to stabilize the cartridge 22 from rotation when it is placed into the device 20. The shell 24 of the cartridge 22 comprises an upper portion (or upper half) 36, and a lower portion (or lower half) 38.

The volatile composition-containing article of manufacture, such as cartridge 22, is preferably removable from the device, and closed and sealed (that is, the volatile compositions are sealed) so that the volatile compositions are protected from evaporation when the cartridge 22 is removed from the device 20. The term "sealed", as used herein, refers to any attempt to seal, or otherwise cover the volatile materials in order to reduce evaporation of the same. The term "sealed" is, therefore, not limited to embodiments in which the volatile materials are sealed in such a manner that there is absolutely no evaporation. The term "sealed" includes configurations which provide at least a partial barrier to evaporation, and those which provide substantially complete barriers to evaporation.

The volatile composition-containing article of manufacture, such as cartridge 22, can in certain embodiments, be disposable after it is "played". In other embodiments, however, it may be desirable for the volatile composition-containing article of manufacture, such as cartridge 22, to be reusable and replayable after it has been initially "played" and removed from the device, and is then inserted back into or onto the device.

The volatile composition-containing article of manufacture, such as cartridge 22, can as shown in the drawings, comprise a closed structure comprising a cover which has at least one opening 52 therein. Preferably, the at least one opening 52 is configured for the emission of a volatile composition from one of the compartments at a given time. Thus, in one embodiment, the cover, shell 24, has a single opening region therein for the emission of one of the scents. In the embodiment shown in the drawings, the cartridge 22 comprises a single opening region 52 with four openings 52A, 52B, 52C, and 52D, separated by members 54 in a region that is configured for the emission of a single composition. The smaller openings 52A, 52B, 52C, and 52D, can be used to prevent user's from touching the exposed volatile compositions.

The volatile composition-containing article of manufacture, such as cartridge 22, preferably also has one or more sealing mechanisms that seal the volatile compositions from evaporation. The sealing mechanisms can be internal of the outer shell, or external of the outer shell of the article of manufacture. The cartridge 22 can have a removable shipping seal for preventing the volatile compositions from evaporating before first use of the cartridge. In the embodiment shown in the drawings, the cartridge 22 also comprises a sealing mechanism that seals the volatile compositions that are not intended to emit volatile compositions when the article is inserted into or placed on the device and volatile compositions are being emitted from the volatile compositions in one of the receptacles. It also is capable of sealing all the volatile composition receptacles when the article is removed from the device. In the embodiment shown in the drawings, this sealing mechanism can have a sealed position and an opened position, and is of the internal type, residing inside the cartridge shell. The volatile composition-containing receptacles are preferably closed with a single sealing mechanism. This single sealing mechanism preferably has only one element thereof that is moved in order to seal all of the receptacles.

The volatile composition-containing article of manufacture, such as cartridge 22, preferably also comprises a locking mechanism which is capable of locking and unlocking the article of manufacture. The locking mechanism preferably prevents access to the volatile compositions when the cartridge 22 is removed from the device for safety purposes. The locking mechanism preferably cooperates with the sealing mechanism. The sealing mechanism has a first sealed position and a second opened position. In the embodiment shown in the drawings, the article of manufacture preferably cannot be removed from the device until the sealing mechanism is in its first sealed position. The article of manufacture preferably also comprises a "blank" section which does not have any volatile compositions provided thereon or therein. The "blank" section provides a start and stop position for emitting volatile compositions from the article of manufacture.

Figure 8:
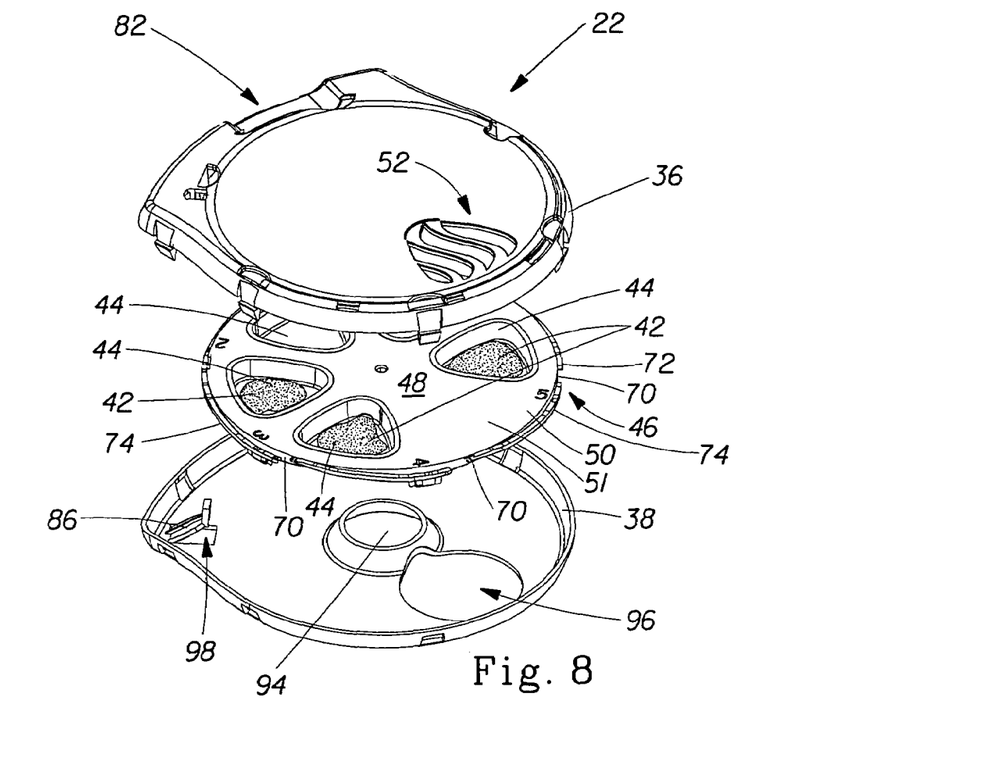
FIG. 8 is an exploded perspective view showing the components of the cartridge shown in FIG. 3.
Figure 9:
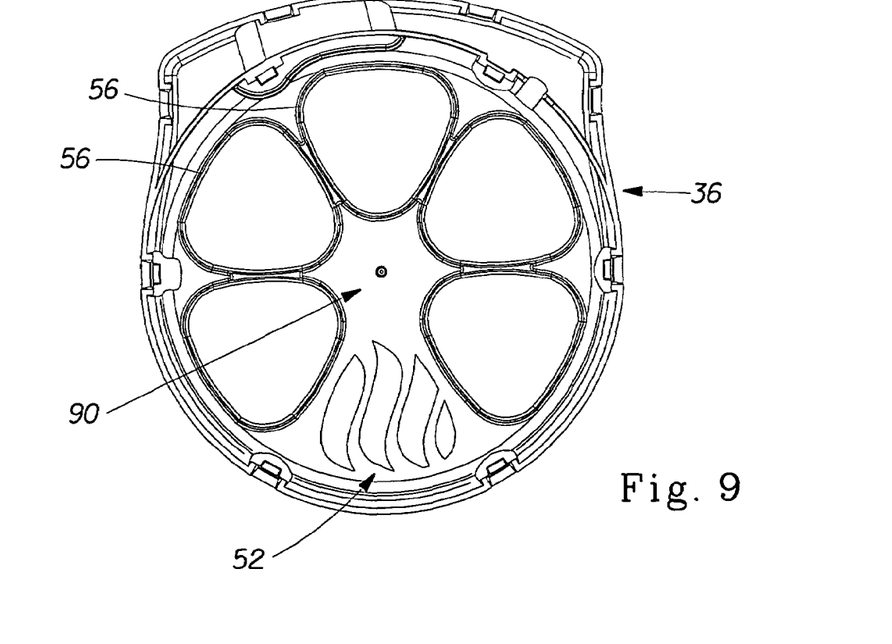
FIG. 9 is a plan view of the underside of the shell comprising the upper half of the cartridge.

FIG. 8 shows the construction of this embodiment of the cartridge 22 in greater detail. In this regard, however, it should be understood that the cartridge 22 shown in FIG. 8 is but one possible embodiment of the article of manufacture. Other types of volatile composition-containing articles can be provided which may not have some or all of the features of the cartridge 22 shown in FIG. 8. The cartridge 22 shown in FIG. 8 comprises several basic components. These include, from top to bottom: the upper part of the cartridge shell 36; a circular rotatable disk or tray 46; and the lower part of the cartridge shell 38. The rotatable tray 46 will be discussed first since, in this embodiment, the other components of the cartridge 22 are designed to cooperate with various features of the tray 46.

The cartridge 22, in one version of this embodiment, contains multiple volatile compositions (or scents, aromatic materials, fragrances, or perfumes) 42 that are disposed on (and/or preferably integrated into) a multiple volatile composition-containing component. Preferably, the multiple volatile compositions are disposed on or in the multiple volatile composition-containing component to form an integral structure. In the embodiment shown in the drawings, the multiple volatile composition-containing component is a circular rotatable tray 46, and the volatile compositions are disposed in receptacles or holders, such as depressions, reservoirs, or pockets 44 formed in the rotatable tray 46.

This tray 46 is contained inside the shell of the cartridge 24 between the upper portion 36 and lower portion 38 thereof. The tray 46 has a top surface 48 and a bottom surface 50. The top surface 48 of the tray 46 has the pockets 44 formed therein. Any suitable number of pockets 44 can be provided, and the pockets 44 can be in any suitable shape. In the embodiment shown in the drawings, there are five pockets 44, and a blank space 51 between two of the pockets 44 for when the cartridge 22 is not intended to emit scents. In the embodiment shown in the drawings, the pockets 44 are in the shape of triangles with rounded corners. The pockets 44 for the volatile compositions in the embodiment shown in the drawings, provide one opening, a top opening, for contact with and emission into the air flowing over the top opening.

In the embodiment shown in FIG. 8, the tray 46 preferably has a plurality of slots 70 in the perimeter 72 thereof. The slots 70 are located at one edge of the scent pockets 44. On either side of these slots 70, are ramps 74 that gradually increase in depth as the slots 70 are approached. In this embodiment of the cartridge 22, the inside surface 90 of the upper portion 36 of the cartridge shell has raised seals 56 for sealing at least some, and preferably all, of the pockets 44 in the tray 46. The raised seals 56 can have any suitable configuration. In the embodiment shown, the raised seals have a configuration similar to that of the perimeter of the pockets 44.

Figure 5:
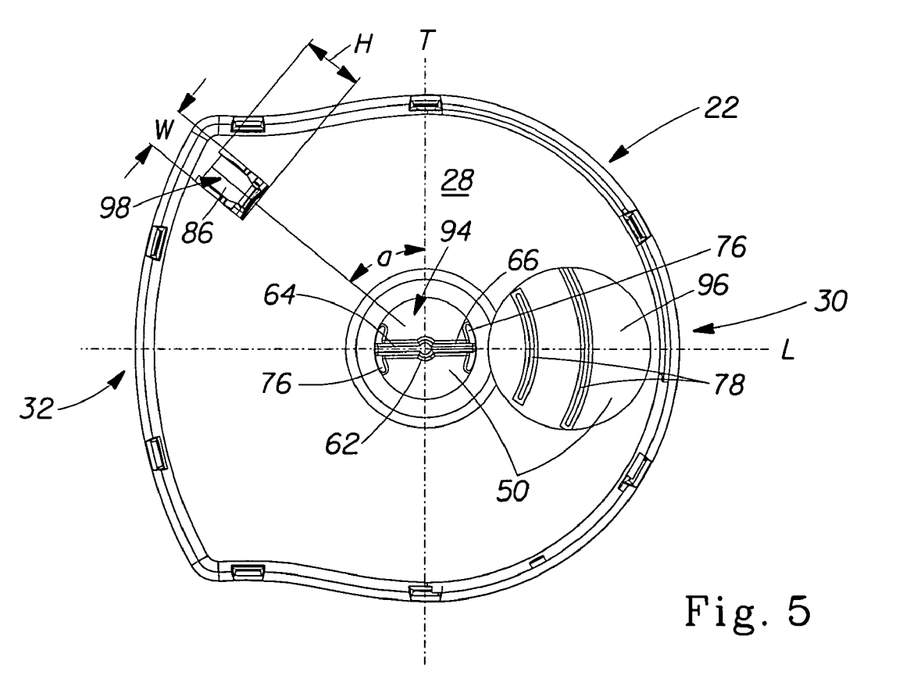
FIG. 5 is a bottom plan view of the cartridge shown in FIG. 3.
Figure 6:
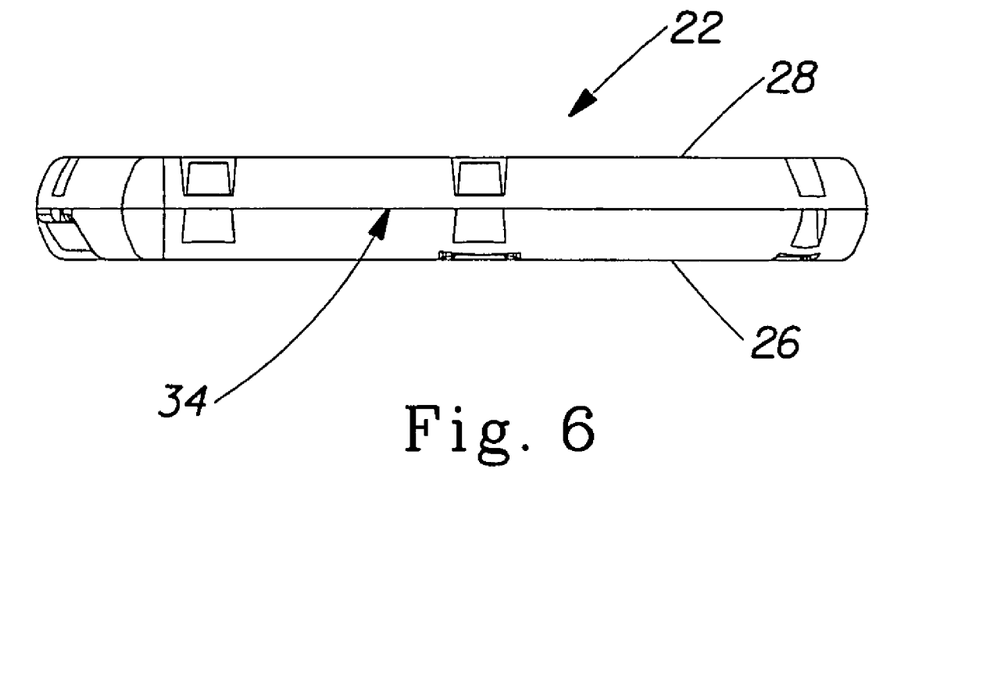
FIG. 6 is a side view of the cartridge shown in FIG. 3.
Figure 7:
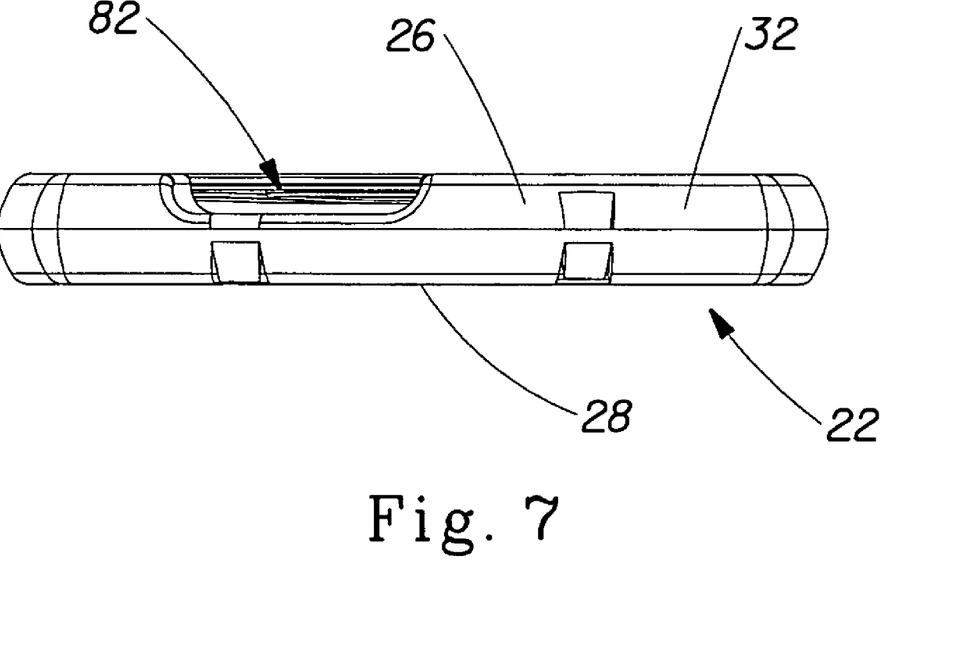
FIG. 7 is a rear view of the cartridge shown in FIG. 3.

As shown in FIGS. 5 and 8, in this embodiment, the cartridge 22 has three openings in its bottom surface 28 (that is, in the lower portion 38 of the cartridge shell). The openings in the lower portion 38 of the cartridge shell include: an opening in the center 94 to provide access for an element of the device to turn the rotatable tray 46 inside the cartridge 22; an opening 96 to allow heat from a heating element in the device 20 to transfer to the volatile composition pocket 44 that is exposed for emission; and an opening 98 to allow the device 20 to activate and deactivate a locking system inside the cartridge 22 for sealing the volatile compositions when the cartridge 22 is not in use. In the embodiment shown, the locking mechanism is a cantilever tab 86 extending from the lower portion of the cartridge shell, and is positioned to meet with the slots 70 around the perimeter of the tray 46 to prevent the tray 46 from rotating. The locking mechanism is, thus, integrated into the cartridge shell and/or the tray 46, and no other components are required. Optional components, such as a metal spring to counteract any creep in the tab 86 may be added if desired, however.

These openings can have any suitable configurations. In the embodiment shown, the opening in the center 94 is circular. In addition, as shown in FIG. 8, the adjacent portion of the cartridge shell forms side walls 58 that extend inward and taper inwardly toward the center of the cartridge 22. These tapered side walls 58 can be used to assist in centering the cartridge 22 on top of the spindle (or hub) 60 of the device when the cartridge 22 is inserted into the device 20. In the embodiment shown, the second opening 96 is also circular. In other embodiments, however, this opening can be configured to mate with the shape of the heating element 142 to further stabilize the cartridge 22 against rotation. In the embodiment shown, the third opening 98 has sides formed of at least some rectilinear segments.

The top surface 26 of the upper portion 36 of the cartridge can have any suitable configuration. The top surface 26 can be flat, convex, or concave. In some embodiments, it may be desirable for the top surface to be slightly convex or concave, so that when the tray 46 and top surface 26 of the cartridge are pushed together, the top surface 26 of the cartridge 22 will flatten. This arrangement may be used to provide a more uniform and predictable sealing surface than a top surface 26 that is initially flat. In the embodiment shown, where the ramps 74 are located around the periphery of the tray 46, it is desirable for the top surface 26 of the cartridge to be concave. Then as the tray 46 is pushed up when it moves on the ramps 74 to form the seal, the top surface 26 of the cartridge 22 will flatten out and the seals 56 on the underside 90 of the upper cartridge shell 36 will make contact with the area around each pocket on the top surface of the tray 46. In embodiments in which the cam system (i.e., the ramps, etc.) is in the center of the tray 46, it may be desirable for the top surface 26 of the cartridge to be convex.

If the cartridge 22 is used in a device 20 comprising a heater, the tray 46 should comprise a material that will not melt when the volatile material(s) are heated. Any suitable material that that satisfies this requirement can be used in such a situation, including, but not limited to polybutyl terapthalate (or "PBT").

The cartridge 22 may be provided with a number of additional features. For example, in some embodiments, the cartridge 22 may be provided with features that ensure that the tray 46 rotates smoothly about a vertical axis therein (without wobbling, or the like). In some embodiments, the cartridge 22 may be provided with features to ensure that the cartridge 22 remains in a fixed position in the device (without rotating or the like) so that the tray 46 inside the cartridge 22 can rotate properly. In some embodiments, the cartridge 22 (or a component thereof, such as the disk 46) may be provided with various safety features (for example, to ensure that the cartridge 22 is inserted properly into the device).

As shown in FIG. 5, in this embodiment, the bottom surface 50 of the tray 46 has several elements projecting therefrom (in addition to the projections formed by the pockets 44). These are shown projecting through holes 94 and 96 in the bottom surface 28 of the cartridge 22. In the center of the tray 46 is a boss 62 having a circular cross-section. The circular boss 62 has one or more ribs extending therefrom, such as ribs 64 and 66 extending from opposing sides thereof. In the embodiment shown, the ribs 64 and 66 have a generally rectangular configuration. In the embodiment shown, the ribs are configured so that one rib 64 is wider than the other rib 66. These ribs 64 and 66 mate with a channel on the top of the hub 60 of the device 20. The configuration of the ribs 64 and 66 is established so that the cartridge 22 can only be inserted into the device 20 in one orientation. The ribs 64 and 66 can be of any suitable size and shape provided that they are capable of ensuring this one way fit. In one non-limiting embodiment, the rib 66 on the side near the blank section of the tray 46 is between about 0.05 inches and about 0.1 inches (about 1.3 to about 2.5 mm) thick. The opposite rib 64 is between about 0.06 inches and about 0.125 inches (about 1.5 to about 3.8 mm) thick. Each rib 64 and 66 protrudes from the center boss 62 between about 0.2 inches and about 0.3 inches (about 60 mm to about 90 mm). Of course, in other embodiments of the device and cartridge, the device and cartridge need not be provided with features that ensure one way fit of the cartridge into the device.

At the ends of the ribs 64 and 66, there can be an arcuate rib 76 that is perpendicular to the ribs. In this embodiment, the rib end and arcuate ribs 76 are sized so that they meet with the portions of the cartridge 22 that define the central hole 94 in the bottom 28 of the cartridge 22. This stabilizes the tray 46 with respect to the bottom of the cartridge to ensure that the tray 46 rotates around a fixed axis within the cartridge 22. Additional arcs or locating features can be added to further stabilize the tray 46 with respect to the cartridge. For example, the bottom surface 50 of the tray 46 may also have other projections, such as large arcuate ribs 78 that underlie the blank section 51 to ensure that the tray 46 rotates smoothly even in the area where no pockets 44 are present.

In the embodiment shown, the sealing mechanism comprises cam followers (or posts) which are shown in the form of horizontally-oriented tabs or shelves and cams (or ramps) that engage with each other to cause components of the cartridge to fit closely together form the seal. The posts 92 and the ramps 74 can be located on any suitable components of the article of manufacture. For example, the posts 92 may be located on the shell 24 and the ramps 74 may be located on the perimeter 72 of the tray 46. In the embodiment shown, the posts 92 are located on the inside portion 90 of the upper shell. In other embodiments, the posts 92 may be located on the lower portion 38 of the cartridge shell. In other embodiments, the locations of the posts 92 and the ramps 74 may be reversed (the posts 92 may be on the tray 46 and the ramps 74 may be on the shell 24). As the tray 46 is rotated into the position where no volatile composition pocket 44 is exposed, the ramps 74 on the perimeter 72 of the tray 46 engage with the posts 92 on inside 90 of the upper shell 36 forcing the tray 46 toward the top surface of the upper shell 36. The top surface 26 of the upper shell 36 is slightly concave and has seals 56 in the same shape as, but larger than the pockets 44 on the tray 46. As the tray 46 moves closer to the inside 90 of the top surface 26 of the upper shell 36, it first makes contact with the center of the inside 90 of the top surface 26 and continues to push the top surface 26 until it changes to a flat configuration when each of the seals 56 make contact with the inside 90 of the top surface 48 of the tray 46.

Figure 10:
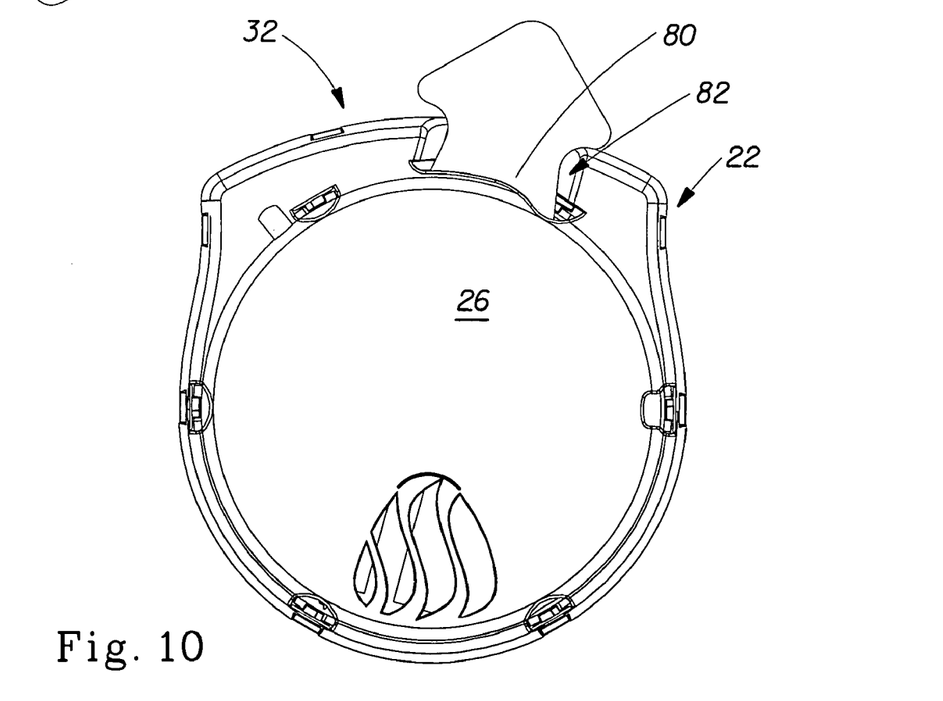
FIG. 10 is a top view of the cartridge shown in FIG. 3 with a portion of a removable sealing material extending from the rear of the cartridge.
Figure 11:
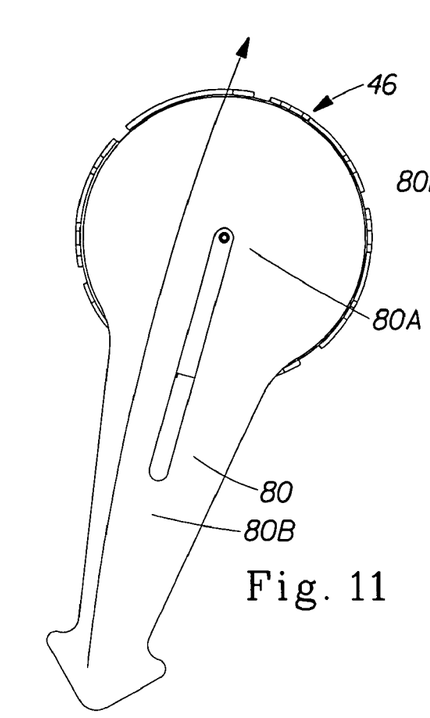
FIG. 11 is a schematic top view showing a first step in applying the removable sealing material to cover the components of the tray of the cartridge.
Figure 12:
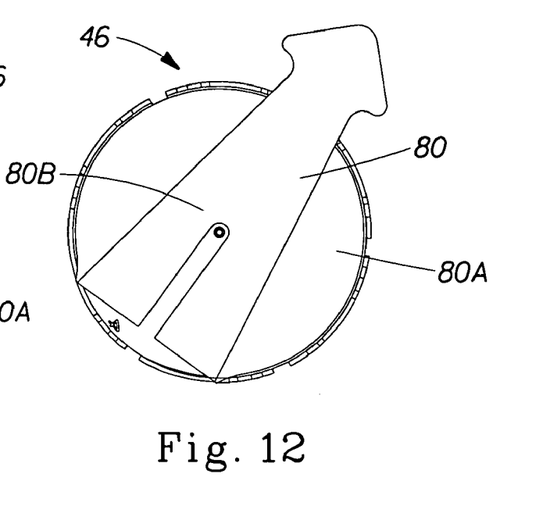
FIG. 12 is a schematic top view showing a second step of folding back a portion of the removable sealing material that covers the components of the tray of the cartridge.

The article of manufacture 22 comprises a shipping seal 80. The shipping seal 80 can be used for example, after the article of manufacture is made, while the article of manufacture is in inventory waiting to be shipped and/or during shipping. It may be desirable to use a shipping seal to provide a tighter seal than can be provided using the cartridge sealing mechanism. FIGS. 10-12 show one non-limiting embodiment of a shipping seal 80. As shown in FIG. 11, the shipping seal 80 comprises at least one piece of material that covers one or more of compartments, such as the pockets 44. The shipping seal 80 can cover any number of compartments, including, but not limited to: two or more, three or more, etc.

The shipping seal 80 can comprise any suitable material, and can be affixed to any part of the article of manufacture in any suitable manner. In one non-limiting embodiment, the shipping seal 80 comprises a peelable film comprised of multiple layers, including, but not limited to an amorphous polyester sealant layer and a metalized polyester barrier layer. In this embodiment, the shipping seal 80 is heat sealed around each of the compartments 44 of the tray 46. Sealing around each of the compartments 44 can be used to prevent cross-contamination between different volatile compositions 42 in the compartments 44, if the compartments 44 contain different materials. The shipping seal 80 is sealed to the tray 46 by a heat seal in which at least a portion of the polyester layer is melted. The shipping seal 80 can be adhesively sealed to the tray 46, but heat sealing may be preferred if the compartments 44 contain perfumes because many adhesives do not work well with many perfume components.

The shipping seal 80 in this embodiment has a first portion, sealing portion 80A, and a second folded portion 80B that is folded back on top of the sealing portion 80A. The folded portion 80B may comprise a tab for grasping by a user. This configuration allows the shipping seal 80 to be peeled from the tray 46 and removed through an opening, such as a slot 82 in the back portion of the cartridge 22 with a single motion.

Numerous other embodiments of the volatile composition-containing article of manufacture, e.g., cartridge 22, are possible. Some non-limiting examples of other embodiments that are applicable to the volatile composition-containing article of manufacture described herein are discussed in greater detail in several of the priority applications that are incorporated by reference herein. In these or other embodiments, the article of manufacture, such as the cartridge can be altered so that it has one or more of the following properties: re-usability, refillability, disposability, and recycleability.

The volatile compositions 42 can be provided in any suitable form. In some embodiments, scents are provided by volatile compositions comprising perfume, such as perfume oils, that are incorporated onto or into a suitable carrier. The carriers can be provided in the following non-limiting forms: a solid, a liquid, a paste, a gel, beads, encapsulates, wicks, a carrier material, such as a porous material impregnated with or containing the perfume, and combinations thereof. In some embodiments, the carrier is in the form of a pliable solid which can be melted and have the perfume ingredients added thereto in order to form a composition that is in the form of a pliable solid structure or matrix at room temperature (73° F. (25° C.), 50% RH).

In one embodiment, the composition is formed by combining polyethylene glycol (or "PEG") having a weight average molecular weight that is greater than or equal to about 8,000, hydrogenated castor oil, and a low level of at least one wax, and at least one volatile ingredient. The volatile ingredient(s) can comprise a number of components or compositions, including, but not limited to: fragrances (or perfume oils), flavors, pesticides, repellants, or mixtures thereof.

The composition can be made in any suitable manner. In one non-limiting embodiment, the composition is formed by heating the carrier material (such as PEG) until it melts, and adding the volatile material(s) to the molten PEG. If the carrier is PEG, it will typically melt at about 100° C. to about 120° C. The PEG serves as a solvent for perfume oils, and perfume oils are completely miscible in the same. Addition of the volatile material(s) will quench the PEG to a lower temperature and form a pliable solid when it cools to room temperature. In embodiments in which a structurant is used, the carrier material and the structurant may be mixed and heated so that they melt together. The volatile material(s) can then be added to the molten mixture of the carrier and structurant. In embodiments in which a wax is used, the carrier material, the structurant, and the wax are mixed and heated so that they melt together. The volatile material(s) can then be added to the molten mixture of the carrier, structurant, and wax.

The structure (or matrix) comprising the composition can be thermally triggered or otherwise energized to emit the volatile material(s).

In certain embodiments, it is desirable for the composition to be heated to a temperature that is in excess of the melting point of the carrier. The addition of perfume ingredients will typically lower the melting temperature of the composition. As perfume ingredients are volatilized, the melting temperature of the remaining portion of the composition will increase. If the composition is always heated to a melting temperature above that of the carrier, then this will always provide sufficient energy to the composition in order to emit the volatile components therefrom.

III. The Device.

Figure 2:
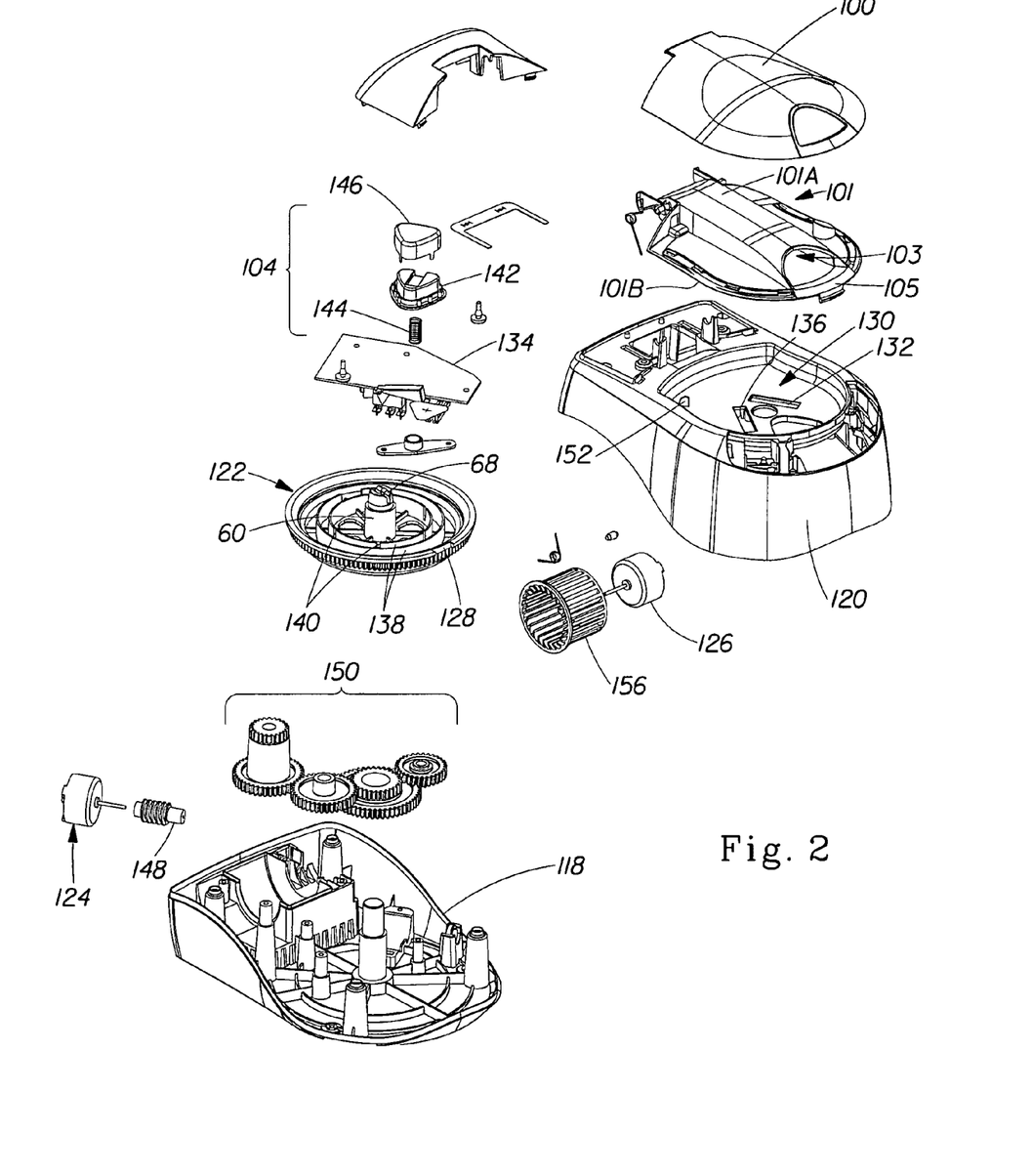
FIG. 2 is an exploded perspective view of the major components of the device shown in FIG. 1.

The scent emitting device (or apparatus, diffuser, or simply the "device") 20 can be in any suitable configuration. One embodiment of the device 20 is shown in FIGS. 1 and 2. In the embodiment shown in the drawings, the shape of the device 20 when viewed from above, is similar to that of the cartridge 22. The device 20 has a top surface 106, a bottom surface 108, a front portion 110, a back or rear portion 112, and sides 114. However, the rear portion of the device 20 extends further than the protrusion 35 on the rear of the cartridge 22. The top of the device has a lid 100 and air discharge outlet 102 thereon. The lid 100 can be transparent so that the user of the device can seen the cartridge 22 inside, and any information thereon.

The device 20 can be configured so that it emits volatile materials, such as scented materials, for an individual's personal use (e.g., the device just emits scents via a tube or the like that is placed in the vicinity of the user's nose), or it can be configured to distribute the volatile materials throughout a particular space, such as a room, or a vehicle, or the like. Preferably, the device 20 is configured to distribute the volatile materials throughout a space.

Numerous other embodiments of the device are possible. It should be understood that the present invention is not limited to devices having the configuration shown in the drawings, and in other embodiments, the configuration of the device can differ greatly from that shown in the drawings.

The device 20 may contain a component for activating the volatile materials from their "resting" state to an activated state. Such a component may include, but is not limited to a component that volatilizes or heats the volatile materials. The dispensing device 20 may also contain a component, such as a fan, for diffusing or transporting the volatile materials into the environment or atmosphere.

FIG. 2 shows the construction of the device 20 shown in FIG. 1. The embodiment of the device 20 shown in FIG. 2 comprises a housing 116 comprising several primary elements including a base 118, a housing body 120, a two piece top cover system (or "cover") which includes the outer lid 100 and an inner lid 101, which can be lifted in unison to receive the cartridge 22, the air discharge outlet 102, a rotating platter 122, and at least one motor (two motors 124 and 126 are included in the embodiment shown in FIG. 2). The device 20 also includes an activating component such as a heater 104 to accelerate diffusion of the volatile materials, and a diffusing component such as a fan 134 to flow forced air through the air discharge outlet over the exposed pocket 44A of volatile materials in the rotatable tray 46. The device 20 may comprise a mechanism for aligning the heating element 142 with one or more of the volatile composition-containing receptacles 44. In one non-limiting embodiment, the mechanism rotates the receptacles 44 within the article of manufacture so as to align at least one of the receptacles 44 with the heating element 142. In other embodiments, there may be more than one heating element under the receptacles 44. In still other embodiments, the receptacles 44 may remain stationary, and the device 20 may comprise a mechanism for rotating or otherwise moving the heating element 142 to align it with the receptacles 44. The inner lid 101 has a top side 101A, an underside 101B, an air flow channel 103, and a front portion 105 that defines the lower portion of the air discharge outlet 102. The outer lid 100 of the two piece cover system is present primarily for aesthetic purposes. The device 20 would function equally well with a single component lid.

The platter 122 further comprises a spindle or hub 60 for engaging and rotating the rotatable tray 46 inside the cartridge 22. In addition, there is a slot 128 in the platter 122 that allows the lid 100 to be opened and the cartridge 22 to be ejected when the platter 122 is in its home position (with the blank space 51 on the tray 46 under the opening region 52 of the cartridge). When the platter 122 is not in the home position, the eject mechanism intereferes with the platter 122 to lock the lid 100 in a closed position. Only when this slot 128 is present (home position), can the eject mechanism move to allow the lid 100 to open. This ensures that the cartridge 22 cannot be removed if a volatile composition-containing pocket 44 is exposed. This also prohibits the user from coming in direct contact with the heating element while it is in the energized state.

When the cartridge 22 is placed inside the device 20, and the cover 100 is closed, the underside 101B of the inner lid 101 and the top surface 26 of the cartridge 22 cooperate to form the air flow channel 103 therebetween. That is, the underside 101B of the inner lid 101 forms the upper portion of the air flow channel 103, and the top surface 26 of the cartridge 22 forms the lower portion of the air flow channel.

In this particular embodiment, the air flow channel 103 is flared toward the front portion of the device 20. This can provide the front of the air flow channel 103 with a nozzle structure to assist in diffusing the volatile materials. The front of the air flow channel can be flared any suitable amount from an angle of greater than 0 degrees with the longitudinal centerline, L1, to 90°, or more on each side of the longitudinal centerline, L1. In the embodiment shown, the front of the air flow channel flares outward at an angle of about 45° on each side of the longitudinal centerline L1 thereof. In addition, the lower portion of the air discharge outlet 102 may be sloped, such as to angle upward from a horizontal orientation. This can also be used to assist in diffusing the volatile materials. The lower portion of the air discharge outlet 102 can form any suitable upward angle greater than 0 degrees up to 300, or more. In this particular embodiment, the front portion 105 of the inner lid 101 provides the lower portion at the front of the air discharge outlet 102 with a ramp that forms an angle of about 15°.

In this particular embodiment, when the cover is lifted, a recessed area 130 for the cartridge 22 is seen. In the embodiment shown, the recessed area 130 is formed in the top portion of the housing 116. The recessed area 130 can be of any suitable configuration. In some embodiments, such as the one shown in the drawings, it may be desirable for the recessed area 130 to conform to at least a portion of the shape of the cartridge 22 so that the cartridge will be prevented from rotating, or otherwise moving, when the tray 46 inside of the cartridge 22 is rotated by the device 20. In one non-limiting embodiment, the recessed area 46 can have substantially the same shape as the exterior of the cartridge 22.

The device 20 may be provided with various safety features. In the embodiment shown, the device 20 is provided with a safety interlock feature that requires the user to insert the cartridge 22 and shut the lid(s) before the device 20 can be started. In this embodiment, a switch 132, such as a spring-loaded switch, is positioned inside the recessed area 130 on the right side of recessed area to the right of the opening for the hub and the hub 60. The switch 132 is in-line with the power supply on a printed circuit board ("PCB") 134. The safety interlock incorporates an additional spring 136 to the left side of the hub in the recessed area 130 to ensure the device 20 is not activated by the weight of the cartridge 22 alone. Thus, even if the device 20 is in play mode, if the additional spring 136 is released, the switch 132 will immediately shut off the device 20. The additional spring 136 is configured so that a force greater than the weight of the cartridge 22 is required to trigger, or activate the same. The additional spring 136 will only be pushed down and turned on when the lid 100 closes and presses down on the top of the cartridge 22. The spring nature of the interlock switch 132, along with the additional spring 136 may also act as an ejection mechanism to help aid in removal of the cartridge 22 from the device 20.

In the embodiment shown, the platter 122 comprises two arcuate positioning rings 138. The inner positioning ring has five notches 140 representing positions that correspond to the location of the pockets 44 in the tray 46. The outer ring has a single notch 140 that corresponds to the location of the position of the blank space 51 in the tray 46 (the "home position"). The platter 122 is used as a positioning system, which moves the appropriate pocket 44 over the heater 104 and into the forced air flow, while leaving the other pockets 44 in a sealed position. This is accomplished by incorporating two paper sensors onto the printed circuit board 134 (a sending unit and a receiver that are shaped into the configuration of the letter U, which reads whether it can "see" itself or not), together with the notches 140 in the positioning rings 138 on the platter 122. The sensors use infrared, or similar means, to detect the presence of the notches 140. When the sensors see notches 140 in the inner positioning ring, the platter 122, and thus cartridge tray 46 is in one of the five "play" positions. When the notch 140 in the outer positioning ring is seen, the platter 122 is in the home position. The positioning system is described in greater detail in a patent application entitled "Apparatus for Dispersing Volatile Materials Into the Environment" filed on the same date as the present application by The Holmes Group.

The heater 104 can be any suitable heater that is capable of heating the volatile compositions to the desired temperature. The heater 104 preferably comprises a heating element 142, which is the part of the heater that becomes hot. In the embodiment shown, the heating element 142 comprises a cover 146 that can be made of any suitable material, including aluminum or stainless steel. The heater 104 can be run at any suitable temperature, and for any suitable duration. In other embodiments, the heater 104 can be omitted altogether, in which case the scents will be diffused from their "at rest" or unheated state by the fan 156 or any other component which can aid in the volatilization of the volatile materials, i.e. infrared energy, microwaves or the like.

Figure 2A:
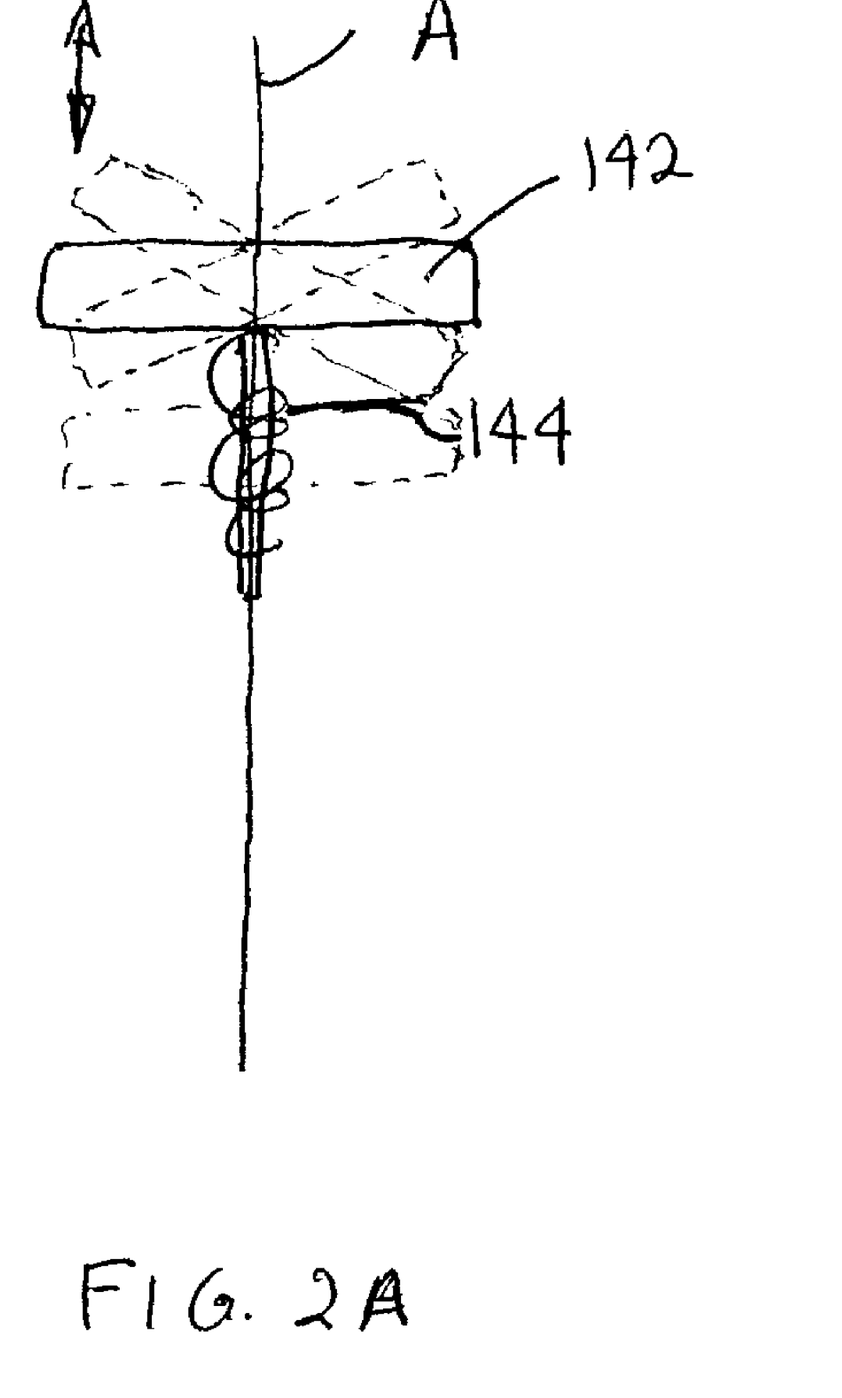
FIG. 2A is a schematic view of the heating element and spring arrangement of the device showing how the heating element can move in phantom.

If a heater is present, the heating element 142 is preferably in proximity to the volatile composition-containing pocket 44A that is exposed for emission. The heating element 142 need not contact the pocket 44A. However, if desired, the heating element 142 may not only be in proximity of the pocket 44A, but may also contact the pocket 44A that is exposed for emission to increase the transfer of heat from the heating element 142 to the volatile composition in the pocket 44A. In the embodiment shown in FIG. 2A, the heating element 142 is configured to be of a "floating" design which allows the heating element 142 to remain in constant contact with the underside of the pocket 44A being heated. This allows heat to be transferred to the volatile composition therein by conduction as opposed to convection. The heating element 142 is positioned on a spring 144 that permits the heating element 142 to move up and down. The connection with the spring 144 may also be configured to allow the heating element 142 to pivot, or tilt from side to side. In the embodiment shown, the center of the heating element 142 remains aligned with a vertical axis, A, but in other embodiments, this can vary.

In this embodiment, the tray 46 inside the cartridge 22 is turned around (rotated) by the hub 60. The channel 68 in the top of the hub 60 engages the ribs 64 and 66 on the underside 50 of the tray 46. The platter 122 is connected to a motor 124 through a series of gears, which comprise a worm gear 148 directly mounted to the motor shaft and a set of gears 150 which then drive the platter 122. The motor 124 rotates the worm gear 148 and the worm gear 148 turns the set of gears 150. The set of gears 150 rotate the platter 122, which turns the tray 46 in the cartridge 22 around.

When the cartridge 22 is outside the device 20, the cartridge 22 will be in a locked position with the blank portion 51 of the rotatable tray 46 in position below the opening 52 in the top portion of the cartridge 22. The rotable tray 46 is locked in the home position via a locking mechanism, such as locking pin 86. This locking pin 86 is part of the lower portion 38 of the cartridge shell. The locking pin 86 fits into a slot 70 on the perimeter 72 of the rotatable tray 46. When the cartridge 22 is placed in the device 20, the locking pin 86 contacts a projection 152 inside the recessed region 130 of the housing of the device. This contact causes the locking pin 86 to be pushed out of the way, allowing the rotatable tray 46 to rotate when it is driven by the hub 60. When the cartridge 22 has been played, and is removed from the device 20, the locking pin 86 prevents the tray 46 from rotating.

In the embodiment shown, the device 20 may have a separate motor 126 for running a fan 156. The motors are wired to the printed circuit board which has the control circuitry, which is linked to the control buttons. The device 20 can be provided with an electrical plug for inserting into an electrical outlet of a structure, vehicle (e.g., automobile cigarette lighter), or the like. Alternatively, the device 20 can be powered with batteries.

The device 20 can have any suitable controls for the user. In some embodiments, the device 20 can have a single control which controls both the activation of the volatile compositions from a resting state to an activated state, and the diffusion of the volatile compositions into the environment. For instance, a single control may control the operation of both the heater 104 and the fan 156. The device 20 can, when it is designed to emit scented volatile compositions, be provided with controls to start and stop the device, to select the scent "volume" or intensity, and to skip one or more volatile compositions in the cartridge. These can include a start and a stop button, which may be separate, but are preferably a single start/stop (or "play") button 160, an eject button or latch 162, a scent intensity control 164, and a "skip" button 168 for skipping ahead to the next scent in sequence. It should be understood that the controls described in the preceding sentence are merely one embodiment of the possible controls for the device 20. The device 20 need not have all of these controls, and may have other, or different controls. If the consumer does not utilize the "skip" control, or if the device 20 is not provided with such a control, the volatile materials can be emitted in a predetermined sequence. Such a sequence can include, but is not limited to, emitting the volatile materials sequentially in the order they are arranged around the tray 46.

The device 20 may also have one or more displays so that the user will be able to determine the control settings. Several non-limiting examples of displays include: a scent intensity display, a scent "track" number display, and a scent duration display. The displays may be in any known form. In the embodiment shown in the drawings, the displays are in the form of light emitting diode (LED) displays. In the embodiment shown in FIG. 1, the play button 160 has a light 166 to indicate when the device 20 is on, and three lights 170 for indicating whether the intensity setting is low, medium, or high. Additionally, the device in FIG. 1 provides a window in the lid 100 to allow the user to see the track number which is illustrated on the rotatable tray 46 of the scent cartridge 22.

The components of the device 20 can be made out of any suitable material, and can be in any suitable arrangement. Suitable materials include, but are not limited to metals (e.g., aluminum), glass, or plastic. Preferably, the duct work on the device, such as the air flow channel 103, is made of PET because it has minimal tendency to absorb odors and deform when heated. In addition, the discharge outlet, the heating element 142, and the scent receptacle 44A for the scent being emitted are preferably located relatively close to the exterior of the device so as to minimize any tendency for scents to contaminate portions of the device which are "down wind" of the discharge outlet 102.

The device 20 may be provided with various internal controls, and other features. In the embodiment shown, for example, the device 20 is provided with a closed loop temperature control (or feedback) system. The closed loop control system can be constantly measuring and adjusting the temperature of the heating element 142 when the device 20 is turned on. This can be achieved in a variety of different ways. For example, the system can comprise a temperature measuring device and a temperature adjusting device. The temperature measuring device can include, but is not limited to: a thermocouple, a thermister, or a resistance temperature detector (RTD); and, the temperature adjusting device can include, but is not limited to a control circuit. In the embodiment shown, a thermister (or thermocouple) is maintained in direct contact with the heating element 142. The thermister constantly measures the temperature of the heating element 142, and adjusts the voltage (or average power) so that the desired heating element 142 temperature is maintained. More specifically, the thermistor is an adjustable resistor that changes resistance as the temperature changes. The printed circuit board, in conjunction with the micro-controller which contains the software program, measures this change and adjusts the power to the heating element 142 accordingly to achieve the target temperature. This can allow the temperature of the heating element 142 to be adjusted to compensate for changes in environmental, and other conditions. It also allows the heater 104 to quickly change from one intensity to another. Other control embodiments could also be used. For example, the temperature could be controlled by predetermining the voltage supplied to the heater needed to reach a certain temperature, or the like. Additionally, this thermistor is integrated into the safety of the device, as the device will not rotate to the home position until the heater is below a safe temperature. This, along with the eject lock and the power interlock prevent the user from coming into contact with an energized heating element. Lastly, a one shot fuse is incorporated into the heater assembly to prevent a situation wherein the heater gets out of the safe operating temperature. In this case, the fuse blows and the device is deenergized.

The device 20 and article of manufacture, such as cartridge 22, can be provided with various features to ensure that only authorized types of articles of manufacture can be inserted into the device 20. For example, in one embodiment, the device 20 may be configured to only receive articles of manufacture that are less than 4.2 inches (10.7 cm) in width. In the case of articles having a circular plan view shape, such articles should have a radius of less than 2.1 inches (5.3 cm). Regardless of the shape of the article, the article may have at least some region, such as at least one of the protrusion regions 35, that can further stabilize the article against rotation in the device 20. These stabilizing regions can begin at a distance of between about 0.9 inches (about 2.3 cm) and about 1.1 inches (about 2.8 cm) from the transverse centerline, T, measured in a direction perpendicular to the transverse centerline T. The article should be no more than about 0.5 inch (about 1.3 cm) in thickness at distances of greater than or equal to about 0.85 inch (about 2.2 cm) from the longitudinal centerline, L, of the article. Due to the airflow channel, 103 defined by the inner lid of the device 20, the article may have a greater thickness in a region along the longitudinal centerline, L. This region of greater thickness can be in an area that is centered about the longitudinal centerline, L, and is between about 1.4 inches (about 3.6 cm) and about 1.7 inches (about 4.3 cm) wide. In one embodiment, the region of greater thickness can be up to about 1 inch (about 2.5 cm) thick, or more.

The article should have a central hole in its bottom that has a minimum diameter of about ½ inch (about 1.3 cm). The article should have an opening on the bottom for the heating element 142 that is at least about 1 inch (about 2.54 cm), preferably at least about 1.25 inch (about 3.2 cm) in width at some portion of the width of this bottom opening. The article should also have a third opening in its bottom for the projection 152 that unlocks the locking pin. At least a portion of this third opening is located in a region that, when viewing the bottom of the article, is at an angle relative to the transverse centerline T, of the article as measured from the intersection of the longitudinal and transverse centerlines, L and T. (The longitudinal and transverse centerlines, L and T, preferably intersect in a region that contains the circular boss 62 on the underside of the tray 46, or any equivalent element that is midway between elements such as ribs 64 and 66 that engage with the channel 68 in the hub 60 of the device. As shown in FIG. 5, the angle, $\alpha$, that this third opening makes relative to the transverse centerline T, is between about 45° and about 55°. At least a portion of the third opening is spaced from about 1.8 inches (about 4.6 cm) and about 2 inches (about 5 cm) from the intersection of the longitudinal and transverse centerlines, L and T. At least a portion of this third opening has a width, W, that is at least about 0.05 inches (about 0.13 cm) up to about 0.36 inches (about 0.9 cm), or more and a height, H, of at least equal size, that can range up to 0.5 inch (about 1.3 cm), or more.

The device 20 can also be provided with instructions for the operation thereof. Such instructions include, but are not limited to placement instructions to ensure and enhance the operation of the device. Placement instructions can include, but are not limited to instructions that instruct the user to: place the device in a location that is not at too low, or too high of a level (e.g., not on the floor; between 2-4 feet (approx. 1 meter +/−30 cm) above the floor); place the device on a hard surface (such as a table or countertop); place the device so that the discharge outlet faces the center of the room, or other area in which the device is placed; and to place the device so that the air flow therefrom will be in the same direction of the natural air flow in the space in which it is placed (e.g., in a two story house, the air flow will typically move toward the stairs going to the second floor). The instructions may also include instructions for setting the intensity based on the size of the room, vehicle, etc. in which the device is placed. The instructions can be provided in any suitable form, e.g., written, audio, and/or video.

The manner in which device may be programmed to emit the volatile materials (the "emission program"), as well as the user input to the same, is discussed in greater detail in several of the applications to which the present application claims priority. The device can also be provided with a non-limiting number of other optional features, if desired. These are also described in several of the prior patent applications.

In addition, numerous other embodiments of the device are possible. For example, it is also contemplated that other embodiments can be made in which the cartridge is located on the outside of the housing of the device during use.

In these or other embodiments, instead of the cartridge having a rotatable disk, the disk could remain stationary and the device can be provided with one or more heating elements (or a plurality of heaters) that lie under, or rotate under the volatile composition-containing receptacles. Of course, in any of the embodiments described herein, the heater could be disposed over, or adjacent to the volatile composition-containing receptacles in other embodiments. Other embodiments are also possible.

The intended mode of operation is for the user to place a cartridge 22 into the device 20 and to close the door and press the play button 160. When the cartridge 22 is outside the device, the cartridge 22 will be in a locked position with the blank portion 51 of the rotatable disk with no scent receptacle therein in position below the opening 52 in the top portion of the cartridge 22. The device 20 will first unlock the rotatable tray 46 inside the cartridge 22 and then will rotate the internal rotatable tray 46 in the cartridge 22 to expose the first pocket 44A containing scent gels. The heating element 142 below the pocket 44A will energize and accelerate the emission of perfume. The fan 156 will then be started, forcing air through the air flow channel 103 and past the exposed pocket 44A containing the volatile composition. This air will then enter the room and diffuse the scent quickly throughout the environment. After a pre-determined interval, the heating will be stopped and the tray 46 will be rotated to expose the next pocket 44. The heater 104 will then restart and emit the next volatile material.

When the user wants to turn the device 20 off, the play/stop button 160 is pressed and the device 20 first rotates the tray 46 inside the cartridge 22 back to the closed position so none of the pockets 44 are exposed to the outside. After this has been completed, the cover can be opened and the user may remove the cartridge. Thereafter, the cartridge 22 may be re-used at a later time if there is still perfume left inside the pockets.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:

1. A system for sequentially emitting more than one differently scented volatile materials, said system comprising: an article of manufacture comprising a cartridge which is a rotatable tray comprising compartments for containing and preventing cross-contamination of said differently scented volatile materials, said article of manufacture comprising a cover; a device for emitting said volatile materials from said article of manufacture, said device comprising a housing, wherein a portion of said housing and at least a portion of the cover of said article of manufacture together define an air flow path for emitting said volatile materials from said device, said device further comprising a heater for sequentially volatilizing and emitting said volatile materials as said compartments in said tray become aligned with said heater, said heater being responsive to temperature and adjustable to provide different temperatures during operation and being controlled by a control system to change from a first temperature to a second temperature during operation and said device yet further comprising a fan so as to facilitate diffusion of said volatile materials into the environment, and further wherein said device additionally includes a safety interlock comprising a spring-loaded switch in-line with a power supply and an additional spring configured so that a force greater than the weight of said cartridge is required to activate said cartridge.

2. The system of claim 1 wherein said first temperature is greater than said second temperature and wherein said heater heats said device to said first temperature prior to heating said device to said second temperature.

3. The system of claim 1 wherein said heater provides for more than two temperatures.

* * * * *